United States Patent [19]
Woollam et al.

[11] Patent Number: 5,582,646
[45] Date of Patent: Dec. 10, 1996

[54] ELLIPSOMETER/POLARIMETER BASED PROCESS MONITOR AND CONTROL SYSTEM SUITABLE FOR SIMULTANEOUS RETROFIT ON MOLECULAR BEAM EPITAXY SYSTEM RHEED/LEED INTERFACE SYSTEM, AND METHOD OF USE

[75] Inventors: John A. Woollam; Blaine D. Johs, both of Lincoln, Nebr.; Peter P. Chow, Minnetonka, Minn.

[73] Assignee: J.A. Woollam Co. Inc., Lincoln, Nebr.

[21] Appl. No.: 327,107

[22] Filed: Oct. 21, 1994

[51] Int. Cl.$^6$ ............................ C23C 14/24; C23C 14/54
[52] U.S. Cl. .................. 118/708; 118/712; 437/7; 437/8; 117/85
[58] Field of Search ................ 437/7, 8; 117/69, 117/85; 118/712, 708

[56] References Cited

U.S. PATENT DOCUMENTS

| | | |
|---|---|---|
| 4,770,895 | 9/1988 | Hartley . |
| 5,096,533 | 3/1992 | Igarashi ........................ 437/8 |
| 5,232,547 | 8/1993 | Drowley et al. ............... 117/85 |
| 5,399,521 | 3/1995 | Celli et al. ..................... 117/85 |
| 5,463,977 | 11/1995 | Manada et al. ............... 117/85 |

FOREIGN PATENT DOCUMENTS

| | | | |
|---|---|---|---|
| 2035635 | 2/1987 | Japan ............................ | 117/85 |
| 6089860 | 3/1994 | Japan ............................ | 117/85 |

OTHER PUBLICATIONS

Ellipsometry & Polarized light, Azzam & Bashara, North–Holland 1977 (exerpts included).
Variable Angle of Incidence Spectroscopic Ellipsometry: Application To GaAs–Al$_x$Ga$_{1-x}$ As Multiple Hetrostructures, J. App. Physics vol. 60(9), Nov. 1986 by Snyder et al.
Encyclopedia of Materials Characterization, Editors Brundle, Evans Jr., Wilson, Articles on RHEED & LEED included ( REED Publushing 1992).

Primary Examiner—Richard Bueker
Attorney, Agent, or Firm—James D. Welch

[57] ABSTRACT

A method of, and system for, applying light beam producing systems such as ellipsometers, polarimeters, polarized light reflectance and functionally similar systems, such that a beam of light produced thereby is caused to be incident upon a process element at an angle in excess of an associated Brewster angle while enabling the production of a signal sufficiently sensitive to changes in process element parameters, for use in "real-time" process element process monitoring and control, is disclosed. In addition a process element processing system and electron beam producing system and light beam producing system combination system is taught, wherein the electron beam producing and light beam producing systems are mounted to the process element processing system, (typically a (MBE) system), by input and output interface systems present at a location appropriate for conventional Reflection High Energy Electron Diffraction (RHEED) systems.

24 Claims, 3 Drawing Sheets

ELLIPSOMETER/POLARIMETER BASED PROCESS MONITOR AND CONTROL SYSTEM SUITABLE FOR SIMULTANEOUS RETROFIT ON MOLECULAR BEAM EPITAXY SYSTEM RHEED/LEED INTERFACE SYSTEM, AND METHOD OF USE

TECHNICAL FIELD

The present invention relates to process element processing systems, and more particularly to process element processing systems which utilize, for instance, Ellipsometer (E) or Polarimeter (P) systems as the source of process monitor and control signals. In its preferred embodiment a spectroscopic ellipsometer (SE) retro-fits by present invention input and output interface systems at an existing Reflection High Energy Electron Diffraction (RHEED) system interface system location on a Molecular Beam Epitaxy (MBE) system, such that during use a (SE) produced beam of light is incident upon a process element in said (MBE) system at an angle typically used in (RHEED) systems, which incident angle is typically well in excess of the (SE) Brewster angle associated with the process element.

BACKGROUND

It is well known to utilize, for instance, Molecular Beam Epitaxy (MBE) systems to deposit epitaxial layers upon process elements such as semiconductor substrates. It is also well known to utilize Reflection High Energy Electron Diffraction (RHEED) and Low Energy Electron Diffraction (LEED) systems, mounted to (MBE) systems at manufacture, as a source of "real-time" signals for use in monitoring and possibly controlling (MBE) epitaxial layer deposition rates.

Briefly, a (MBE) system is comprised of a vacuum chamber in which one or more effusion cells are present, and into which vacuum chamber can be placed a process element. During use thereof said effusion cells serve as the source of elements or compounds etc. which are to be deposited as an epitaxial layer upon said process element. When "real-time" monitor and/or control of the thickness or rate of an epitaxial layer deposition upon a process element in an (MBE) system is required a (RHEED) or (LEED) system is commonly mounted to said (MBE) system such that a beam of electrons is caused thereby to impinge upon said substrate at a glancing, (eg. typically at an eight-eight degree angle to the normal to said process element for (RHEED) systems and a considerably lesser angle for (LEED) systems), incident angle and be reflected into a detection System wherein a signal is produced which can be used to monitor deposition rate, possibly control effusion cell operation and/or terminate the deposition etc. It is emphasised that (MBE) systems are commonly fitted with electron diffraction (RHEED) systems at manufacture.

It is to be appreciated that "real-time" signals for use in monitoring and in the control of epitaxial deposition in (MBE) systems can also be derived from Ellipsometer (E) and Polarimeter (P) systems, and that signals from such systems can provide information regarding not only deposited epitaxial layer growth rate and thickness, but also composition, roughness and even the temperature thereof during deposition. It is emphasised that Ellipsometer derived signals can be easily utilized in process control with respect to a number of process element parameters. Signals from (RHEED) systems, however, typically provide monitoring information regarding epitaxial layer deposition rate and thickness only within a limited range and are rarely used in a control mode. While benefits of utilizing (E) and (P) systems rather than (RHEED) systems are thus identified, a problem exists in interfacing (E), (P) and (MBE) systems because major and costly, (in terms of time and money), modifications must typically be made to a standard (MBE) system to allow application of (E), (P) or functionally similar systems thereto so that a beam of light produced thereby can be caused to impinge upon a process element therein at an optimum angle of incidence, near the Brewster angle. (Those skilled in the art of ellipsometry will understand the reference to the Brewster angle to identify that angle of incidence at which the Rp component of a polarized beam of light reflected from a process element, as monitored by intensity measurements, becomes a minimum and in some cases essentially zero (0) while the Rs component remains a relatively large percentage, (eg. 35%+), as compared to respective incident beam intensities). Accepted teachings and understanding of those with ordinary skill in the art of (E) applications are that any deviation from a Brewster angle of incidence, (especially an angle greater than the Brewster angle as measured with respect to a normal to a process element), lead to reduced (E) process element parameter change (eg. epitaxial deposition), detection sensitivity. That is, no known teachings remotely suggest that an (E) system should be applied to monitoring, for instance, epitaxial deposition upon a process element in "real-time", wherein the angle at which a produced beam of light is caused to be incident upon a process element significantly exceeds the Brewster angle. A book by Azzam and Bashara titled "Ellipsometry and Polarized Light", published by North Holland, 1989 makes this very clear, as does a paper by Snyder et al. titled "Variable angle of Incidence Spectroscopic Ellipsometer: Application to GaAs-AlxGal-x As Multiple Hetrostructures", J. App. Physics, Vol. 60(9), 1986. The summary of said paper states " . . . the sensitivity of Delta was found to be strongly peaked near the principal angle, . . . ". (Note that the "Principal angle" is, for the purposes of this Disclosure, to be interpreted as being simply alternate terminology for "Brewster angle").

In addition, inspection of a patent to Hartley, U.S. Pat. No. 4,770,895, shows very well that conventional understanding in the relevant art provides that a Spectroscopic Ellipsometer (SE) system should be oriented so that a polarized light beam produced thereby is incident at a less glancing angle to a process element surface during use, than is a beam of electrons from a (RHEED) system.

In summary, when a single wavelength polarized beam of light is-incident upon a process element, sensitivity to epitaxial layer thickness and other parameters achievable by an (E), (P) or functionally similar system has typically been observed to decrease when the angle of incidence thereof upon a process element exceeds the Brewster angle.

Continuing, recent developments in (SE) technology have allowed the Inventors of the present invention to apply and detect a multiplicity of polarized light beam wavelengths simultaneously. This capability allowed the Inventors of the present invention to discover the extremely surprising result that when a multiwavelength (SE) polarized beam of light is impinged upon a process element at an incident angle of from approximately seventy-eight (78) to eighty-five (85) degrees to a normal to said process element, (which later incident angle is comparable to that at which electron beams are incident upon process elements by (RHEED) systems, and which incident angle is well beyond the Brewster angle associated with (SE) systems for typical substrates), signals derivable from certain of the wavelengths present provide acceptably good sensitivity to changes in process element parameters of interest such as process element thickness, composition, surface roughness and temperature. That is, even when the angle of incidence of a (SE) polarized beam of light is beyond the Brewster angle, (which for the case of semiconductor process elements is approximately seventy-five (75) degrees), some wavelengths in a multiwavelength beam of light can be utilized in development of strong signals appropriate for use in real-time monitoring and control of (MBE) epitaxial deposition because they demonstrate adequate high sensitivity to changes in said process element parameters, control of which is desired. It is noted that as epitaxial layers are grown or material composition changes, the wavelengths giving optimum signals in (SE) and functionally similar systems may change. However, there will generally be one or more wavelengths, perhaps closely bunched or perhaps distinctly separated, which demonstrate good sensitivity.

Because of the superior process element parameter detection capabilities of (E) systems as compared to (RHEED) systems, which superior detection capabilities were alluded to infra, it should be clear that utility would be provided by use of (E) systems in development of signals appropriate for use in the control of epitaxial layer deposition in (MBE) systems. Until recently however, application of (E) systems to typical (MBE) systems was thought to require an (E) system oriented with respect to a (MBE) system such that a polarized beam of light produced thereby was caused to be incident upon a process element therein at or very near the Brewster angle with respect thereto. Retro-fit of (SE) systems to existing (MBE) systems, again as alluded to infra, is as a result, typically expensive and time consuming, and risks contamination of the (MBE) chamber with impurities.

The present invention is found in the extremely surprizing discovery that an (E) system can be retro-fitted to existing (MBE) systems utilizing existing (RHEED) or (LEED) interface systems and successfully utilized when so oriented to produce signals which can be utilized in the monitor and control of epitaxial deposition onto process elements in said (MBE) system. This, of course, forces use of such a retro-fitted (E) system in a mode wherein the angle of incidence of a polarized beam of light produced thereby, upon said process element, greatly exceeds the Brewster angle where the process element is a semiconductor. The present invention, however, teaches that proper selection of one or more wavelengths from a multiplicity of wavelengths present in a beam of light, (preferably polarized), so incident, allows use of a (SE) system in development of signals appropriate for use in monitor and control of (MBE) system operation. In view of conventional knowledge and practice in the area of (SE) systems and applications thereof, this is a very surprising discovery. The present invention then makes possible an approach to simple economical retro-fit application of (E) and functionally similar systems to existing process element processing systems (eg. (MBE) systems), which are, at manufacture, fitted with, for instance, (RHEED) or (LEED) systems. The present invention provides an unexpected, easily implemented, solution to a long felt need. Said need being best demonstrated as a simple cost effective application of (E) systems, preferably (SE) systems, to (MBE) systems which are not designed for use therewith at manufacture.

The present invention is not to be considered as limited to retro-fit application in (MBE) systems which are initially manufactured with (RHEED) interface systems present. Even in the case of new (MBE) systems combining (RHEED) and (SE) ports simplifies the construction and preserves valuable space in the (MBE) chamber which otherwise has to be used to mount the (SE) to allow use at the Brewster angle. As well, the method of the present invention can be practiced even in the absence of an (MBE) system.

It is also to be understood that (RHEED) and (LEED) systems require a vacuum through which a produced beam of electrons is caused to flow toward a process element. Light Beams do not require a vacuum, hence, a (MBE) system utilizing a (E) or functionally similar system can have the vacuum present therewithin selected based singularly upon effusion cell operation requirements.

The present invention is suitable for use with process elements such as semiconductors, crystals of superconductors, optoelectronics, ferroelectric materials etc.

Finally, the reader is referred to the cited book by Azzam and Bashara, (incorporated by reference herein), and other standard references for insight to ellipsometry, spectroscopic ellipsometry, polarimetry, polarized light reflectance and other light beam producing source based techniques. It is directly stated however that all techniques involve the impinging of a light beam comprised of one or more wavelengths upon a process element, and monitoring changes in the light beam effected by interaction therewith. Ellipsometry utilizes polarized light and effected changes in orthoganally related Rp and Rs components, (and ratios thereof), are investigated. Polarimetry is a very much similar technique but in which rotational direction of the light beam polarization is also important. A technique termed Polarized Light Reflectance utilizes only one of the Rp and Rs components of a polarized light beam. Spectroscopic Ellipsometry involves use of a multiplicity of wavelengths simultaneously. Any light beam based technique which utilizes single or multiple wavelength polarized or nonpolarized light is to be considered within the scope of the present invention.

DISCLOSURE OF THE INVENTION

The system of the present invention is, in its most easily understood and preferred embodiment, a combined Reflection High Energy Electron Diffraction (RHEED) or Low Energy Electron Diffraction (LEED) system and Ellipsometer (E), (preferably a Spectroscopic Ellipsometer (SE)), system in combination with a process element processing system such as a Molecular Beam Epitaxy (MBE) system, said combination being effected by an interface system which allows simultaneous presence of (RHEED) or (LEED) and (E) systems at an essentially common location on said (MBE) system. It is to be understood that the present invention can be practiced with a Polarimeter (P) system or Polarized Light Reflectance system in place of the (E) system and that generally, any particle and light beam producing systems and process element processing systems can comprise the system of the present invention. The present invention can specifically comprise a molecular beam epitaxy system in combination with a light beam producing system affixed thereto via particle beam producing interface systems, with or without a particle beam producing system present.

The method of the present invention can be implemented other than in combination with process element processing (eg. (MBE)), systems and need not necessarily be present in combination with a (RHEED), (LEED) or functionally similar system. That is, the present invention is, in its purest form, a method of practicing light beam investigation of process elements, typically during processing thereof, by for instance, Ellipsometry, (preferably spectroscopic), Polarimetry, Polarized Light Reflectance or functionally similar methods which involve application of a beam of light, (preferably but not necessarily polarized), produced by a light beam producing system and applied at an angle of incidence to a process element under analysis, which angle of incidence is significantly greater than the Brewster, (see Background Section), angle associated with said process element.

The present invention is found primarily in the very surprising result that a light beam source, (eg. (E) or (P) system), can be used to develop a signal which can be very successfully applied in "real-time" to monitor and control of a process, such as epitaxial growth upon, (or etching of), a process element in a (MBE) or functionally similar system, when the angle at which a beam of light produced by said (E) or (P) system is caused to be incident upon said process element is significantly in excess of the Brewster, or alternatively termed, "Principal", angle. That is, the present invention teaches that a signal, (eg. changes in ellipsometric PSI or DELTA values), so derived can provide sufficient sensitivity to changes in process element parameters under investigation to allow use in process monitoring and control. The key to successfully practicing the present invention is found in proper selection of the wavelength(s) of light utilized.

Conventional wisdom guides those who practice ellipsometry and polarimetry to configure an (E), (P) or functionally similar system so that the angle of incidence of a beam of light produced thereby is incident upon a process element to be analyzed, at, or very close to the Brewster angle. It is at this angle of incidence that the largest sensitivity of a produced signal, with respect to change in a process element parameter, can be achieved thereby. Conventional wisdom provides no suggestion that an angle significantly greater than the Brewster angle should be utilized, and in fact teaches away therefrom. The present invention, however, in the face of conventional understanding, teaches that an angle significantly larger than the Brewster angle can, and in certain circumstances, (as taught by the present invention), should be utilized, emphasis added.

The present invention was discovered by the inventors thereof as the result of observations made possible by recent advances in the area of Spectroscopic Ellipsometers (SE's). The inventors of the present invention, having simultaneous access to the signals provided by numerous wavelengths in a beam of light produced by a (SE) system and applied to a process element, noted that sufficient sensitivity to changes in process element parameters under investigation during a processing procedure, was available in certain light beam wavelengths, when the angle of incidence of the light beam to a process element under investigation was significantly in excess of the Brewster angle. While said sensitivity was not the maximum achievable at the Brewster angle, a signal derived therefrom was found to be sufficient for use in "real-time" process monitoring and control.

The preferred embodiment of the present invention then is primarily a method of practicing ellipsometry and polarimetry in which the angle of incidence of a beam of light produced by a light beam source (eg. (E) or (P)), system is incident upon a process element at an angle greatly in excess of the Brewster angle. Said method involving the steps of:

a. selecting one or more wavelength(s) of light to comprise a beam of light provided by a light beam production system (eg. (E) or (P) and functionally similar), system, which wavelength(s) provide usable sensitivity to changes in one or more process element parameter(s) under investigation, when said beam of light is applied thereto at an angle of incidence greatly in excess of the Brewster angle, and b. deriving a signal from changes in said beam of light comprised of one or more wavelength(s), which changes result from interaction with said process element, for application in process element process monitoring and control.

Any source of polarized or unpolarized light beams, can be utilized in the practice of said method, including those which utilize only the Rp or Rs component of a polarized beam of light, (such as a Polarized Light Reflectance system).

It is also noted that a computer simulation program is commercially available from J. A. Woollam Co. called WVASE (Registered Trademark), which aids a practitioner of ellipsometry and polarimetry in selection of appropriate wavelengths based upon assumed process element parameters such as composition, number of layers, surface and interfacial roughness, alloy materials present, non-uniformity, index of refraction, extinction coefficient, angle of light beam incidence etc. The present invention utilizes this program to predict appropriate wavelengths for use in investigation of certain process element parameters. For instance, it should be understood that a certain wavelength might serve to allow investigation of a process element while it is in some band of process states, but not in other bands of process states. Advance expectation of this can greatly aid practice of the present invention.

The system of the present invention is an interface system which allows simultaneous application of particle beam production, (eg. (RHEED), (LEED) and functionally similar), systems and light beam production systems, (eg. (E), (P) and functionally similar), systems to an (MBE) or functionally equivalent system at a location on said (MBE) or functionally equivalent system corresponding to a typical particle beam production system, (eg. (RHEED)), interface system.

The present invention will be better understood by reference to the Detailed Description Section of this Disclosure in conjunction with the accompanying Drawings.

SUMMARY OF THE INVENTION

Conventional wisdom in the practice of ellipsometry and polarimetry is that a beam of light produced by an ellipsometer or polarimeter system should be caused to incident upon a process element at an angle as close as possible to the Brewster angle. This is the case as light beam parameters (eg. ellipsometry PSI and DELTA), show greatest sensitivity to changes in investigated process element parameters when incident on a process element at the Brewster angle.

In addition, typical Molecular Beam Epitaxy (MBE) systems provide an interface system that allows fitting and application of a Reflected High Energy Electron Diffraction (RHEED) and/or Low Energy Electron Diffraction (LEED) system, which (RHEED) and/or (LEED) is typically utilized in development of "real-time" signals for use in process monitoring and control.

Typical electron diffraction (RHEED) systems interface to (MBE) systems such that electron beams produced thereby are caused to be incident upon a process element present in a (MBE) system at an angle which is greatly in excess of the Brewster angle of Ellipsometer (E) and Polarimeter (P) systems.

Conventional wisdom in the practice of ellipsometry is, as mentioned however, that the angle of incidence of a beam of light produced by an (E) or (P) system should not greatly exceed the Brewster angle.

The present invention is based in the discovery that appropriate selection of the wavelength(s) of light which comprise a beam of light produced by a Spectroscopic Ellipsometer (SE) system allows use of a (SE) system oriented with respect to a process element under investigation such that the angle of incidence of said beam of light is greatly in excess of the Brewster angle. That is, sufficient sensitivity in a signal derived from application of said (SE) system operated with a light beam comprised of appropriate wavelengths can be developed with respect to changes in process element parameter changes to allow application of an (SE) system in which the angle of incidence of said light beam is greatly in excess of the Brewster angle.

It is noted that a simulation program which allows a practitioner of ellipsometry and polarimetry to select appropriate wavelengths, called WVASE (Registered Trademark) is available from J. A. Woollam Co. in Lincoln, Nebr.

It is to be understood that the present invention system can comprise any light beam production system in combination with any process element processing system and that practice of the method of the present invention, in its most basic form, does not require a process element processing system be present.

It is therefore a purpose of the present invention to teach a method of practicing ellipsometry, polarimetry and like methods in which the angle of incidence of a beam of light, (produced by, for instance, an ellipsometer or polarimeter system), upon a process element under investigation is greatly in excess of the Brewster angle.

It is another purpose of the present invention to teach that proper selection of the wavelength(s) of light present in a beam of light produced by, for instance, an ellipsometer system, (preferably a spectroscopic ellipsometer system), or polarimeter or functionally similar system allow attainment of sufficient sensitivity in, for instance, ellipsometry PSI and DELTA parameters, to changes in process element parameters under investigation, to allow use thereof in "real-time" process monitoring or control when said beam of light is incident upon a process element at an angle greatly in excess of the Brewster angle.

It is yet another purpose of the present invention to teach that an ellipsometer or polarimeter or functionally similar system can be mounted to a process element processing system (eg. an (MBE) system), at an existing interface system present for interfacing a particle beam, (eg. RHEED or LEED), source system thereto and be successfully utilized in process element process monitoring and control.

DETAILED DESCRIPTION

Figure 1:
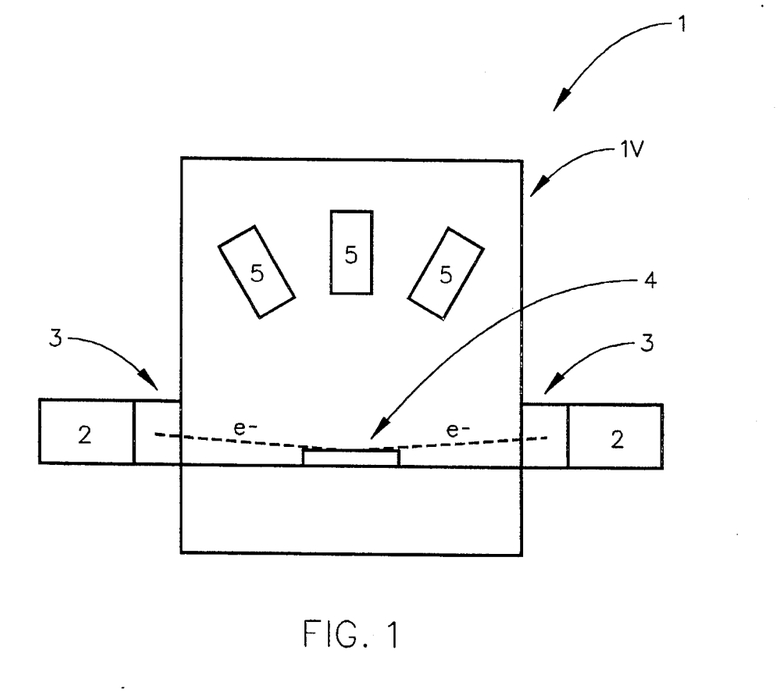
FIG. 1 shows a (MBE) system conventionally fitted with a (RHEED) system.

Turning now to the Drawings, there is shown in FIG. 1, a representation of a Molecular Beam Epitaxy (MBE) system (1). Shown are a Vacuum Chamber (IV) in which are present a number of effusion cells (5) for providing elements and/or compounds etc. in a manner appropriate for deposition upon a process element (4). Shown present at the lower extent of the (MBE) system (1) is a Reflection High Energy Electron Diffraction (RHEED) system (2) although a Low Energy Electron Diffraction (LEED) system might just as well be present thereat. Interface system (3) serves to attach the (RHEED) system (2) to said (MBE) system (1) such that a beam of high energy electrons produced thereby will be incident upon a process element (4) in said (MBE) system (1) at a glancing angle, nominally in the range of eighty-eight (88) degrees to a normal to said process element (4) surface, (slightly less if a (LEED) system is present).

Typical usage of an (MBE) system (1) provides that a vacuum be created in the Vacuum Chamber (1V), and that elements and/or compounds etc. made available by the effusion cells (5) deposit upon process element (4). During use (RHEED) system (2) provides an electron (e-) beam which reflects from the surface of process element (4) in a diffracted form. It is common practice to derive "real-time" signals from said (RHEED) system (2) for use in process monitoring or control. It is emphasised that (MBE) systems (1) are commonly designed and produced at original manufacture with (RHEED) system (2) interface systems (3) present. It is therefore a simple matter to fit a (RHEED) system (2) to a typical (MBE) system (1).

Figure 2:
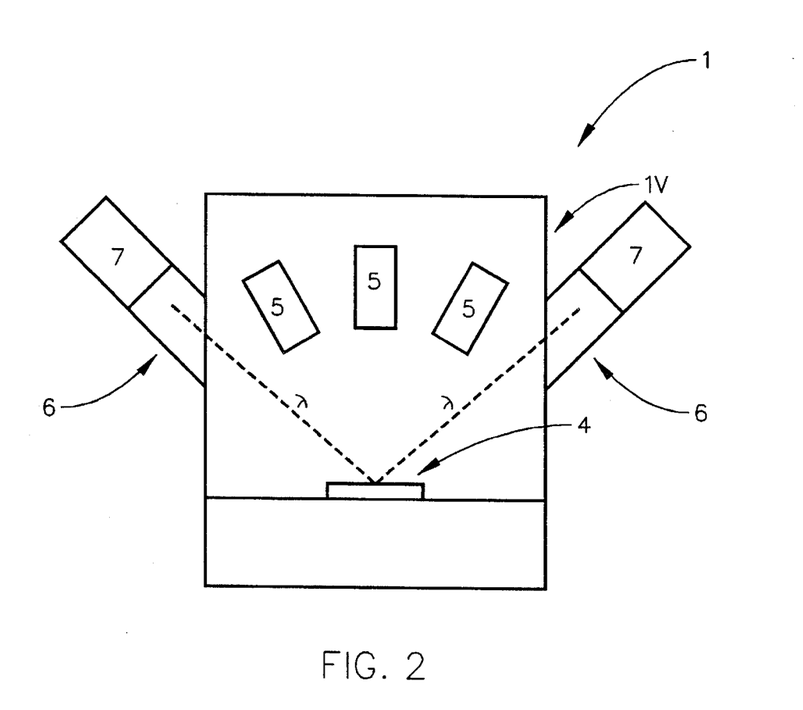
FIG. 2 shows a (MBE) system conventionally fitted with an (E) system.

Turning now to FIG. 2, there is shown a (MBE) system (1) similar to that shown in FIG. 1, but which has an Ellipsometer (E) system (7), preferably a Spectroscopic Ellipsometer (SE) system interfaced thereto by interface system (6). The important thing to observe in FIG. 2 is that the angle at which a beam of light, (identified by the lambda's), is incident upon process element (4) is not as shallow as that at which the electrons (e-) are incident upon a process element (4) as shown in FIG. 1. Conventional wisdom in the area of application of (E) systems (7) is that the angle of incidence should be very near what is termed the Brewster, (see Background Section), angle. In the case where a semiconductor is the process element (4), said angle is typically seventy-five (75) degrees. When a (RHEED) system (2) is utilized and the process element is a semiconductor, the angle of incidence of a beam of electrons is typically eighty-five (85) degrees.

Until the present invention, it was commonly accepted that an (E) system (7) could not be interfaced to an (MBE) system (1) using the same interface system (3) as is used to interface a (RHEED) system (2) thereto. This is because the angle at which a beam of light from the (E) system (7) would by necessity be incident upon a process element (4) at an angle greatly beyond the Brewster angle. Use of such an incident angle causes sensitivity of (E) system (7) developed signals to changes in process element parameters to sharply decrease.

It is the teaching of the present invention, however, that a judicious selection of the wavelength(s) content of a beam of light when practicing ellipsometry allows application of a produced beam of light at an angle greatly beyond the Brewster angle, while still allowing development of a signal which demonstrates sufficient sensitivity to investigated process element parameter changes, to allow said developed signal to be utilized in real time process monitoring and control.

Figure 3:
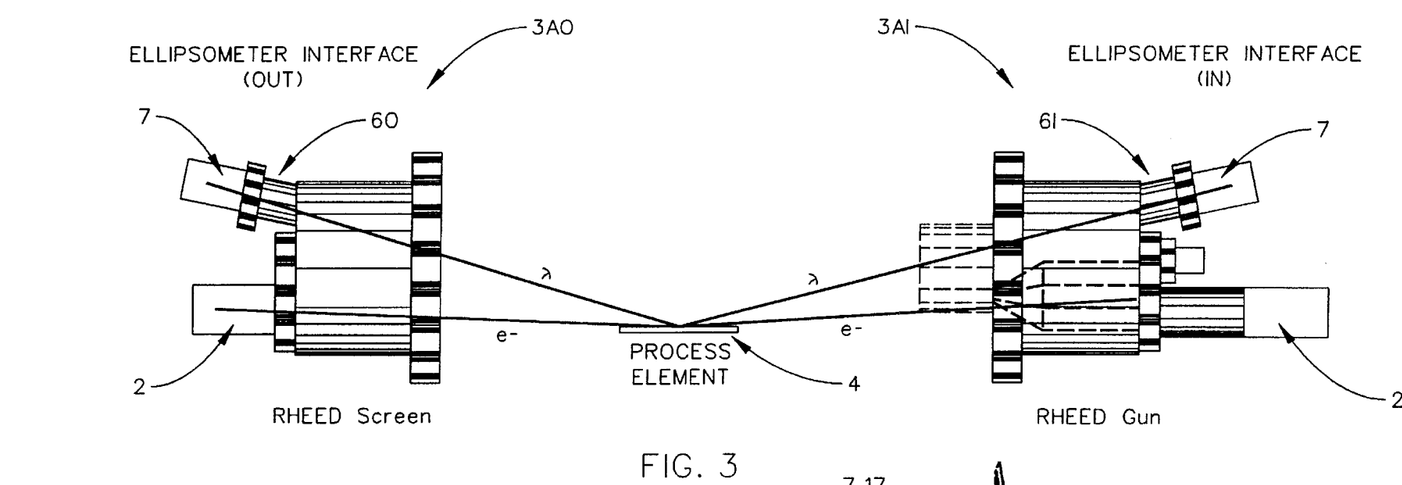
FIG. 3 shows a common (RHEED) and (E) interface system for attachment to a (MBE) system.
Figure 5:
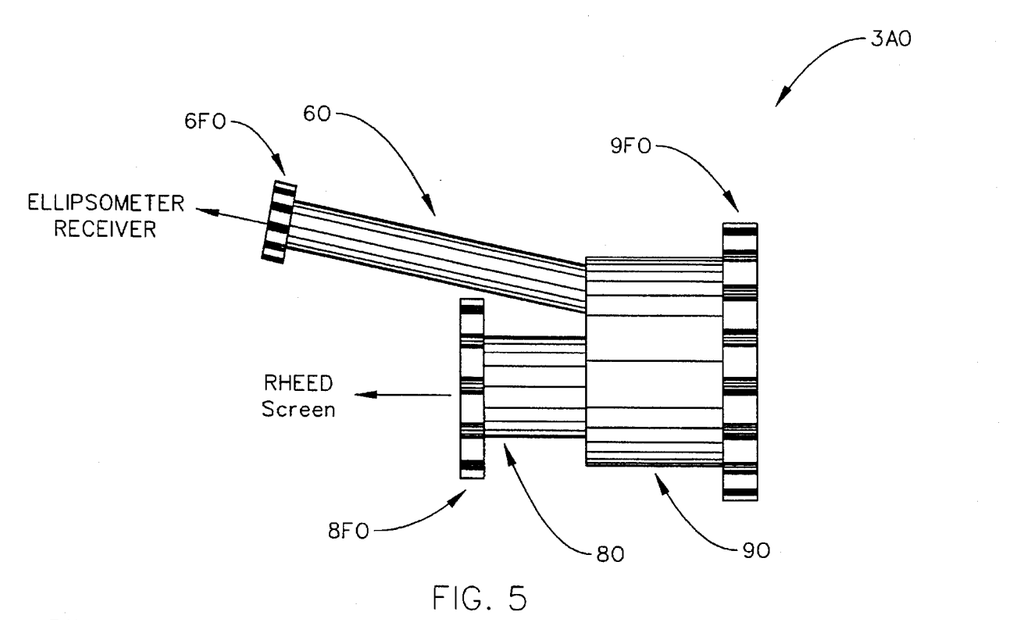
FIG. 5 shows an expanded view of an output side interface system for simultaneously attaching both (RHEED) or (LEED) and (E) or (P) systems to an (MBE) system.
Figure 6:
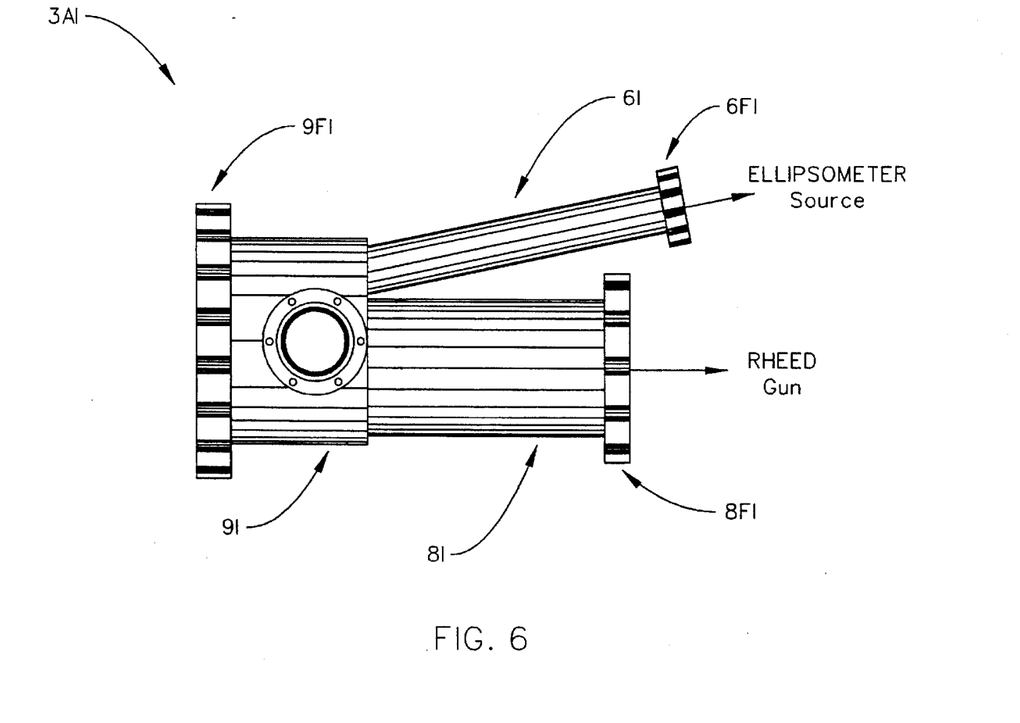
FIG. 6 shows an expanded view of an input side interface system for simultaneously attaching both (RHEED) or (LEED) and (E) or (P) systems to an (MBE) system.

FIG. 3 shows an expanded view of an (MBE) system (1), (RHEED) system (2) interface systems (input (3AI) and output (3AO)), in which (E) system (7) interface systems, (input (6I) and output (6O)), have been incorporated into the modified (RHEED) system (2) interface systems (input (3AI) and output (3AO)). FIG. 3 shows that the angle of incidence of the beam of light, (identified by lambda's), developed by the (E) system (7) and the angle of incidence of the electrons, (e) developed by the (RHEED) system (2) are then caused to be quite similar. That is, the angle of incidence of the light beam greatly exceeds the Brewster angle. FIGS. 5 and 6, discussed supra, show expanded views of the input (3AI) and output (3AO) interface systems of the present invention.

It is the teaching of the present invention that a simultaneous (RHEED) or (LEED) system (2) and (E) system (7) interface such as shown in FIG. 3 can be successfully applied to (MBE) systems (1), and that signals produced by (E) system (7) when so interfaced to an (MBE) system (1) can demonstrate sufficient sensitivity to changes in investigated process element parameter changes so that real-time monitoring and process control signals can be derived therefrom.

Simply stated, the present invention teaches that proper selection of the wavelength content of the beam of light produced by the (E) system (7) allows use of the (E) system (7) oriented so that the beam of light produced thereby is incident upon a process element at an angle greatly in excess of the Brewster angle.

Figure 4:
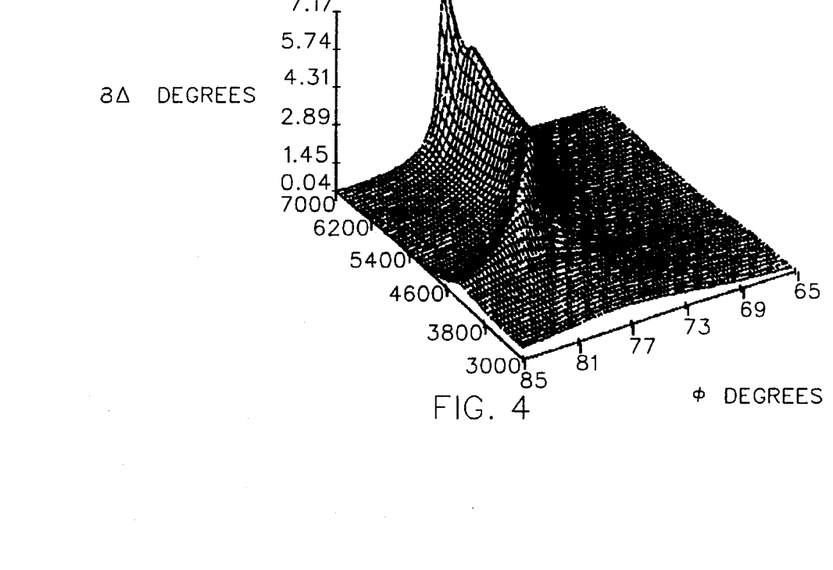
FIG. 4 shows a three-dimensional plot of ellipsometer Delta sensitivity in a (SE) system as a function of incident angle and wavelength.

Turning now to FIG. 4, there is shown a sample three dimensional plot showing actual Sensitivity in an Ellipsometry DELTA value, (shown on "Y" axis), as a function of both wavelength, (shown on "Z" axis), and angle of incidence, (shown on "X" axis), of a beam of light upon a process element. (It is to be understood that different process elements will provide numerically different, but generally similar plots). This sample three dimensional plot demonstrates why the present invention is viable. Note that very pronounced sensitivity is shown to exist at an angle of incidence of approximately seventy-five (75) degrees, (the Brewster angle), for wavelengths in the range of approximately forty-six-hundred (4600) to seven-thousand (7000) Angstroms, but that as the angle of incidence is increased toward eighty-eight (88) degrees, the sensitivity sharply drops. However, note that at approximately forty-five-hundred (4500) Angstroms, sensitivity, though reduced, remains even at an angle of incidence of eighty-five (85) degrees. It is said sensitivity which the present invention teaches should be utilized when a (E) system (7) is interfaced to an (MBE) system (1) at a conventional (RHEED) or (LEED) interface system location, as indicated in FIG. 3.

The present invention then teaches that an (E) system (7), preferably a Spectroscopic Ellipsometer (SE) system, can be applied to the investigation of process element parameter changes when a beam of light produced thereby is incident upon said process element surface at an angle greatly in excess of the Brewster angle, such as is effected when an (E) system (7) is interfaced to a (MBE) system (1) via (RHEED) system (2) modified input and output interface adaptors (3AI) and (3AO). Prudent selection of the wavelength content of said beam of light serves to allow an (E) system (7) to develop and provide a signal which can be utilized in real time process monitoring and control.

FIG. 6 and FIG. 5 show enlarged views of modified (RHEED) interface systems, (input (3AI) and output (3AO) respectively), as identified in FIG. 3. Input (RHEED) interface (3AI) serves to attach a (RHEED) source electron gun, and an Ellipsometer source to an (MBE) chamber. Output (RHEED) interface (3AO) serves to attach a (RHEED) screen and an Ellipsometer Receiver to an (MBE) system. In general, the flanges (9FI) and (9FO) serves to attach the (RHEED) Input Main Nipple Tube (9I) and (RHEED) Screen Main Nipple Tube (9O) adaptors to an (MBE) system. (RHEED) Main Nipple Tube (9I) serves to provide attachments to bifrucated Ellipsometer Window Tube (6I) as well as and (RHEED) Gun Tube (8I), (with flanges (6FI) and (8FI) serving to attach ellipsometer and (RHEED) input system components thereto. (RHEED) Screen Main Nipple Tube (9O) serves to provide attachments to bifrucated Ellipsometer Output Tube (6O) and (RHEED) Screen Tube (8O), with flanges (6FO) and (SFO) serving to attach Ellipsometer and (RHEED) system output components thereto. The various Nipple (9I) and (9O), Input (6I) and (8I) and Output ((6O) and (8O) Ellipsometer and (RHEED) system Tubes are typically circular in cross section. In addition, the Ellipsometer Window Input (6I) and Output (6O) tubes are each oriented at an angle with respect to the corresponding (RHEED) Gun Tube (8FI) and (RHEED) Window Screen Tube (8O) respectively, at a nominal angle of four (4) degrees, although a range of angles from approximately zero (0), (essentially resulting in a combined single tube), to ten (10) degrees is possible.

Equivalent above described interface systems can also be applied to (P), Polarized Light Reflectance and (LEED) interfacing to a (MBE) system.

It is to be understood that for the purposes of Claim construction the terminology "main nipple tube" (9I) (9O), refers to input and output interface systems used with (RHEED), (LEED) and (E), (SE), (P) and/or functionally similar systems generally and which were identified, with specific reference to a (RHEED) system application, in FIGS. 6 and 5, as (RHEED) Input Main Nipple Tube (9I) and (RHEED) Screen Main Nipple Tube (9O) adaptors to an (MBE) system.

It is to be understood that for the purposes of claim construction the terminology "particle beam producing source system tube" (8I) (8O), refers to input and output interface systems used with (RHEED), (LEED) and/or functionally similar systems generally and which were identified, with specific reference to a (RHEED) system application, in FIGS. 6 and 5, as (RHEED) Gun tube (8I) and (RHEED) Screen Tube (8O).

It is to be understood that for the purposes of claim construction the terminology "light beam producing source system tube" (6I) (6O), refers to input and output interface systems used with (E), (SE), (P) and/or functionally similar systems generally and which were identified, with specific reference to an (E) system application, in FIGS. 5 and 6, as Ellipsometer Window Input (6I) and Output (6O) tubes. Said "light beam producing source tube" can comprise a wave guide and/or a optical fiber.

It is emphasised that particle beam producing source system and light beam producing source system tubes are configured so as to converge at an angle of from zero (0) to ten (10) degrees therebetween.

It is to be understood that for the purpose of claim construction the terminology "process element processing system" (1) includes any system such as an (MBE) (1) or any functionally similar system for use in deposition and/or etching a process element, such as a semiconductor substrate.

It is to be understood that the method of the present invention can be practiced in conjunction with, or without, an (MBE) or functionally similar systems generally.

It is also to be understood that the method of the present invention can be carried out using an ellipsometer, (preferably a spectroscopic ellipsometer), a polarimeter, a polarized light reflectance system and/or functionally similar systems generally.

It is also to be understood that the present invention system comprises input (3AI) and output (3AO) interface systems on an (MBE) or functionally similar system for simultaneous attachment of an (E), (P) and/or functionally similar system and a (RHEED), (LEED) and/or functionally similar system, to an (MBE) or functionally similar systems generally.

It is to be understood that for the purposes of claim interpretation the generic terminology "particle beam producing system" refers to (RHEED), (LEED) electron beam producing systems and functionally similar systems, and systems which produce ion beams.

It is to be understood that for the purposes of claim interpretation the generic terminology "light beam producing system" refers to (E), (SE), (P) Polarized Light Reflectance and functionally similar systems.

It is also to be understood that a modifed embodiment of the present invention combines light beam source system and particle beam source system tubes into a single tube, or provides only a single tube, to which is attached at least a light beam producing system and that no tube lenght limitations are imposed, (a tube can be simply two flanges for instance).

It is also to be understood that the term "light" is to be understood to include the entire electromagnetic spectrum.

Having hereby disclosed the subject matter of the present invention, it should be obvious that many modifications, substitutions, and variations of the present invention are possible in light of the teachings. It is therefore to be understood that the invention may be practiced other than as specifically described, and should be limited in breadth and scope only by the claims.

We claim:

1. A process element processing system in combination with a particle beam producing system and a light beam producing system, said particle beam producing and light beam producing systems being mountable simultaneously to said process element processing system via input and output interface systems such that a beam of light produced by said light beam producing system is during use, caused to be incident upon a process element present in said process element processing system at an angle of incidence between a Brewster angle of said present process element and an eighty-eight degree nominal angle of incidence of said particle beam inclusive of said particle beam nominal angle of incidence but exclusive of said Brewster angle, with said light beam angle of incidence further being within ten degrees of said particle beam nominal angle of incidence.

2. A process element processing system in combination with an particle beam producing system and a light beam producing system as in claim 1, in which the particle beam producing system is a reflection high energy electron diffraction system.

3. A process element processing system in combination with an particle beam producing system and a light beam producing system as in claim 1, in which the particle beam producing system is a low energy electron diffraction system.

4. A process element processing system as in claim 1, in which the light beam producing system is an ellipsometer.

5. A process element processing system as in claim 1, in which the light beam producing system is a spectroscopic ellipsometer.

6. A process element processing system as in claim 1, in which the light beam producing system is a polarimeter.

7. A process element processing system as in claim 1 in which the input and output interface systems comprise:

a. a main nipple tube;

b. a particle beam producing source system tube;

c. a light beam producing source system tube;

such that said particle beam producing source system tube and light beam producing source system tube are, at first ends thereof, continuously attached to said main nipple tube, and such that said main nipple tube attaches to said process element processing system at an end thereof not attached to said particle beam producing source and light beam producing source system tubes, which particle beam producing and light beam producing systems can attach to said particle beam producing source system tube and light beam producing source system tube respectively, at an ends thereof not attached to said main nipple tube.

8. A process element processing system as in claim 7 in which said particle beam producing source system and light beam producing source system tubes are combined into a single tube essentially equivalent to the particle beam producing source system tube, to which is mounted at an end thereof not attached to said main nipple tube, at least said light beam producing system.

9. A process element processing system to which is attached a particle beam producing system and a light beam producing system in such proximity and orientation to one another that respective electron and light beams produced thereby and directed toward a process element in said process element processing system impinge thereupon at incident angles between a Brewster angle of said present process element and an eighty-eight degree nominal angle of incidence of said particle beam inclusive of said particle beam nominal angle of incidence but exclusive of said Brewster angle, with said light beam angle of incidence further being within ten degrees of said particle beam nominal angle of incidence.

10. A process element processing system as in claim 9 in which the process element processing system is a molecular beam epitaxy system.

11. A process element processing system as in claim 9, in which the light beam producing system is an ellipsometer.

12. A process element processing system as in claim 9, in which the light beam producing system is a spectroscopic ellipsometer.

13. A process element processing system as in claim 9, in which the light beam producing system is a polarimeter.

14. A process element processing system as in claim 9, in which the particle beam producing system is a reflection high energy electron diffraction system.

15. A process element processing system as in claim 9, in which the particle beam producing system is a low energy electron diffraction system.

16. A process element processing system to which is attached a light beam producing system such that light beams produced thereby and directed toward a process element in said process element processing system impinge thereupon at an incident angle between a Brewster angle of said present process element and an eighty-eight degree nominal angle of incidence of a typical particle beam inclusive of said typical particle beam nominal angle of incidence but exclusive of said Brewster angle, with said light beam angle of incidence further being within ten degrees of said typical particle beam nominal angle of incidence.

17. A process element processing system as in claim 16 in which the process element processing system is a molecular beam epitaxy system.

18. A process element processing system as in claim 16, in which the light beam producing system is an ellipsometer.

19. A process element processing system as in claim 16, in which the light beam producing system is a spectroscopic ellipsometer.

20. A process element processing system as in claim 16, in which the light beam producing system is a polarimeter.

21. A process element processing system in which input and output interface systems comprise light beam producing source system tubes, such that said light beam producing source system tubes, at a first end thereof, attach to said process element processing system at an end thereof not attached to a light beam producing system, which light beam producing system attachs to said light beam producing source system tubes, at ends thereof not attached to said process element processing system, said input and output interface systems being oriented at angles with respect to said process element processing system so as to cause a light beam produced by an attached light beam producing system to impinge upon a process element therein at an angle of incidence between a Brewster angle of said present process element and an eighty-eight degree nominal angle of incidence of a typical particle beam inclusive of said typical particle beam nominal angle of incidence but exclusive of said Brewster angle, with said light beam angle of incidence further being within ten degrees of said typical particle beam nominal angle of incidence.

22. A process element processing system as in claim 21 in which the input and output interface system light beam producing source system tubes comprise flanges.

23. A process element processing system as in claim 21 in which the input and output interface system light beam producing source system tubes comprise optical fibers.

24. A process element processing system as in claim 21 in which the input and output interface system light beam producing source system tubes comprise waveguides.

* * * * *